(12) United States Patent
Ferguson et al.

(10) Patent No.: US 7,029,461 B2
(45) Date of Patent: Apr. 18, 2006

(54) SAFETY SHIELD FOR MEDICAL NEEDLES

(75) Inventors: F. Mark Ferguson, Salt Lake City, UT (US); Kendall P. Thorne, Layton, UT (US)

(73) Assignee: Tyco Healthcare Group LP, Mansfield, MA (US)

( * ) Notice: Subject to any disclaimer, the term of this patent is extended or adjusted under 35 U.S.C. 154(b) by 144 days.

(21) Appl. No.: 10/164,944

(22) Filed: Jun. 6, 2002

(65) Prior Publication Data

Related U.S. Application Data

(63) Continuation-in-part of application No. 09/892,593, filed on Jun. 27, 2001, and a continuation-in-part of application No. 09/619,190, filed on Jul. 19, 2000, now Pat. No. 6,592,556, which is a continuation-in-part of application No. 09/433,449, filed on Nov. 4, 1999, now Pat. No. 6,280,420, and a continuation-in-part of application No. 09/434,036, filed on Nov. 4, 1999, now Pat. No. 6,254,575.

(60) Provisional application No. 60/254,506, filed on Dec. 8, 2000, provisional application No. 60/275,810, filed on Mar. 14, 2001, now abandoned, provisional application No. 60/275,886, filed on Mar. 14, 2001, provisional application No. 60/296,968, filed on Jun. 8, 2001.

(51) Int. Cl.
*A61M 5/32* (2006.01)

(52) U.S. Cl. ................ 604/198; 604/192; 128/919

(58) Field of Classification Search ............. 604/110, 604/164.08, 192, 198, 263; 128/919
See application file for complete search history.

(56) References Cited

U.S. PATENT DOCUMENTS

| 1,779,451 A | 10/1930 | Sponsel | |
|---|---|---|---|
| 2,559,474 A | 7/1951 | Son | 128/215 |
| 2,700,385 A | 1/1955 | Ortiz | 128/215 |
| 2,836,942 A | 6/1958 | Miskel | 53/25 |
| 2,854,976 A | 10/1958 | Heydrich | 128/221 |

(Continued)

FOREIGN PATENT DOCUMENTS

EP      0 144 483      6/1985

(Continued)

*Primary Examiner*—Nicholas D. Lucchesi
*Assistant Examiner*—Catherine S. Williams (57) ABSTRACT

A medical needle shield apparatus is provided which includes an extensible shield having a first segment and a second segment extending therefrom. The second segment includes an opening configured for clearance of a medical needle of a medical needle device during attachment of the extensible shield to the medical needle device. The second segment defines a planar surface adjacent a distal portion thereof. The planar surface is configured to engage the needle for disposing the shield in an extended position. In alternate embodiment, the medical needle shield apparatus has a syringe having a needle hub supporting a needle. The first segment articulates from a collar disposed about the needle hub. The collar includes a pair of latches. The opening is configured for travel about the needle to facilitate extension of the shield from a retracted position to an extended position. The second segment further includes a proximal fulcrum that engages the needle to facilitate extension of the shield. The second segment also has a pair of catches. The catches are engageable with the latches to maintain the shield in the retracted position. The second segment has a nose portion defining a planar surface configured to engage the needle to facilitate fixing the shield in the extended position.

15 Claims, 12 Drawing Sheets

U.S. PATENT DOCUMENTS

| | | | |
|---|---|---|---|
| 2,953,243 A | 9/1960 | Roehr | 206/43 |
| 3,021,942 A | 2/1962 | Hamilton | 206/43 |
| 3,073,307 A | 1/1963 | Stevens | 128/221 |
| 3,074,542 A | 1/1963 | Myerson et al. | 206/43 |
| 3,255,873 A | 6/1966 | Speelman | 206/56 |
| 3,294,231 A | 12/1966 | Vanderbeck | 206/63 |
| 3,323,523 A | 6/1967 | Scislowicz et al. | 128/214 |
| 3,329,146 A | 7/1967 | Waldman, Jr. | 128/221 |
| 3,333,682 A | 8/1967 | Burke | 206/43 |
| 3,367,488 A | 2/1968 | Hamilton | 206/63 |
| 3,485,239 A | 12/1969 | Vanderbeck | 128/218 |
| 3,537,452 A | 11/1970 | Wilks | 128/214 |
| 3,587,575 A | 6/1971 | Lichtenstein | 128/215 |
| 3,610,240 A | 10/1971 | Harautuneian | 128/214 |
| 3,658,061 A | 4/1972 | Hall | 128/214 |
| 3,828,775 A | 8/1974 | Armel | 128/218 |
| 3,840,008 A | 10/1974 | Noiles | 128/221 |
| 3,890,971 A | 6/1975 | Leeson et al. | 128/218 |
| 3,904,033 A | 9/1975 | Haerr | 206/349 |
| 3,934,722 A | 1/1976 | Goldberg | 206/365 |
| 3,968,876 A | 7/1976 | Brookfield | 206/365 |
| 4,040,419 A | 8/1977 | Goldman | 128/215 |
| 4,106,621 A | 8/1978 | Sorenson | 206/365 |
| 4,113,090 A | 9/1978 | Carstens | 206/365 |
| 4,139,009 A | 2/1979 | Alvarez | 128/218 |
| 4,175,008 A | 11/1979 | White | 435/295 |
| 4,270,536 A | 6/1981 | Lemelson | 128/218 |
| 4,300,678 A | 11/1981 | Gyure et al. | 206/364 |
| 4,375,849 A | 3/1983 | Hanifl | 206/366 |
| 4,430,082 A | 2/1984 | Schwabacher | 604/263 |
| 4,592,744 A | 6/1986 | Jagger et al. | 604/192 |
| 4,634,428 A | 1/1987 | Cuu | 604/110 |
| 4,643,722 A | 2/1987 | Smith, Jr. | 604/192 |
| 4,659,330 A | 4/1987 | Nelson et al. | 604/192 |
| 4,664,259 A | 5/1987 | Landis | 206/365 |
| 4,664,654 A | 5/1987 | Strauss | 604/198 |
| 4,681,567 A | 7/1987 | Masters et al. | 604/198 |
| 4,695,274 A | 9/1987 | Fox | 604/198 |
| 4,702,738 A | 10/1987 | Spencer | 604/198 |
| 4,723,943 A | 2/1988 | Spencer | 604/198 |
| 4,728,320 A | 3/1988 | Chen | 604/110 |
| 4,728,321 A | 3/1988 | Chen | 604/110 |
| 4,731,059 A | 3/1988 | Wanderer et al. | 604/192 |
| 4,735,311 A | 4/1988 | Lowe et al. | 206/365 |
| 4,735,618 A | 4/1988 | Hagen | 604/192 |
| 4,737,144 A | 4/1988 | Choksi | 604/198 |
| 4,738,663 A | 4/1988 | Bogan | 604/198 |
| 4,743,233 A | 5/1988 | Schneider | 604/192 |
| 4,747,836 A | 5/1988 | Luther | 604/198 |
| 4,747,837 A | 5/1988 | Hauck | 604/198 |
| 4,772,272 A | 9/1988 | McFarland | 604/198 |
| 4,778,453 A | 10/1988 | Lopez | 604/110 |
| 4,781,697 A | 11/1988 | Slaughter | 604/192 |
| 4,782,841 A | 11/1988 | Lopez | 128/164 |
| 4,790,828 A | 12/1988 | Dombrowski et al. | 604/198 |
| 4,795,432 A | 1/1989 | Karczmer | 604/110 |
| 4,795,443 A | 1/1989 | Permenter et al. | 604/198 |
| 4,801,295 A | 1/1989 | Spencer | 604/198 |
| 4,804,372 A | 2/1989 | Laico et al. | 604/198 |
| 4,813,426 A | 3/1989 | Haber et al. | 128/763 |
| 4,816,022 A | 3/1989 | Poncy | 604/198 |
| 4,816,024 A | 3/1989 | Sitar et al. | 604/192 |
| 4,819,659 A | 4/1989 | Sitar | 128/764 |
| 4,820,277 A | 4/1989 | Norelli | 604/192 |
| 4,826,490 A | 5/1989 | Byrne et al. | 604/198 |
| 4,826,491 A | 5/1989 | Schramm | 604/198 |
| 4,838,871 A | 6/1989 | Luther | 604/192 |
| 4,840,619 A | 6/1989 | Hughes | 604/187 |
| 4,842,587 A | 6/1989 | Poncy | 604/198 |
| 4,846,796 A | 7/1989 | Carrell et al. | 604/110 |
| 4,846,811 A | 7/1989 | Vanderhoof | 604/263 |
| 4,850,968 A | 7/1989 | Romano | 604/110 |
| 4,850,976 A | 7/1989 | Heinrich et al. | 604/192 |
| 4,850,977 A | 7/1989 | Bayless | 604/198 |
| 4,850,978 A | 7/1989 | Dudar et al. | 604/201 |
| 4,850,994 A | 7/1989 | Zerbst et al. | 604/198 |
| 4,850,996 A | 7/1989 | Cree | 604/198 |
| 4,858,607 A | 8/1989 | Jordan et al. | 128/314 |
| 4,863,434 A | 9/1989 | Bayless | 604/198 |
| 4,863,435 A | 9/1989 | Sturman et al. | 604/198 |
| 4,863,436 A | 9/1989 | Glick | 604/198 |
| 4,867,172 A | 9/1989 | Haber et al. | 128/763 |
| 4,867,746 A | 9/1989 | Dufresne | 604/192 |
| 4,872,552 A | 10/1989 | Unger | 206/365 |
| 4,874,382 A | 10/1989 | Lindemann et al. | 604/195 |
| 4,874,383 A | 10/1989 | McNaughton | 604/198 |
| 4,874,384 A | 10/1989 | Nunez | 604/198 |
| 4,883,469 A | 11/1989 | Glazier | 604/192 |
| 4,886,503 A | 12/1989 | Miller | 604/192 |
| 4,887,998 A | 12/1989 | Martin et al. | 604/110 |
| 4,888,001 A | 12/1989 | Schoenberg | 604/162 |
| 4,892,107 A | 1/1990 | Haber | 128/763 |
| 4,892,521 A | 1/1990 | Laico et al. | 604/192 |
| 4,898,589 A | 2/1990 | Dolgin et al. | 604/198 |
| 4,900,309 A | 2/1990 | Netherton et al. | 604/192 |
| 4,904,244 A | 2/1990 | Harsh et al. | 604/187 |
| 4,911,694 A | 3/1990 | Dolan | 604/198 |
| 4,911,706 A | 3/1990 | Levitt | 604/198 |
| 4,927,018 A | 5/1990 | Yang et al. | 206/365 |
| 4,929,241 A | 5/1990 | Kulli | 604/263 |
| 4,935,012 A | 6/1990 | Magre et al. | 604/192 |
| 4,935,013 A | 6/1990 | Haber et al. | 604/192 |
| 4,936,830 A | 6/1990 | Verlier | 604/110 |
| 4,944,397 A | 7/1990 | Miller | 206/365 |
| 4,944,731 A | 7/1990 | Cole | 604/192 |
| 4,950,249 A | 8/1990 | Jagger et al. | 604/192 |
| 4,950,250 A | 8/1990 | Haber et al. | 604/192 |
| 4,978,344 A | 12/1990 | Dombrowski et al. | 604/198 |
| 4,982,842 A | 1/1991 | Hollister | 206/365 |
| 4,985,021 A | 1/1991 | Straw et al. | 604/198 |
| 4,994,041 A | 2/1991 | Dombrowski et al. | 604/164 |
| 5,000,744 A | 3/1991 | Hoffman et al. | 604/232 |
| 5,015,240 A | 5/1991 | Soproni et al. | 604/192 |
| 5,057,089 A | 10/1991 | Greco | 604/198 |
| 5,059,180 A | 10/1991 | McLees | 604/110 |
| 5,092,851 A | 3/1992 | Ragner | 604/192 |
| 5,108,379 A | 4/1992 | Dolgin et al. | 604/198 |
| RE34,045 E | 8/1992 | McFarland | 604/198 |
| 5,135,509 A | 8/1992 | Olliffee | 604/292 |
| 5,139,489 A | 8/1992 | Hollister | 604/192 |
| 5,147,303 A | 9/1992 | Martin | 604/110 |
| 5,154,285 A | 10/1992 | Hollister | 206/365 |
| 5,176,655 A | 1/1993 | McCormick et al. | 604/198 |
| 5,176,656 A | 1/1993 | Bayless | 604/198 |
| 5,193,552 A | 3/1993 | Columbus et al. | 128/760 |
| 5,195,983 A | 3/1993 | Boese | 604/192 |
| 5,209,739 A | 5/1993 | Talalay | 604/195 |
| 5,232,454 A | 8/1993 | Hollister | 604/192 |
| 5,232,455 A | 8/1993 | Hollister | 604/192 |
| 5,242,417 A | 9/1993 | Paudler | 604/192 |
| 5,242,418 A | 9/1993 | Weinstein | 604/192 |
| 5,246,427 A | 9/1993 | Sturman et al. | 604/192 |
| 5,246,428 A | 9/1993 | Falknor | 406/198 |
| 5,250,031 A | 10/1993 | Kaplan et al. | 604/110 |
| 5,254,099 A | 10/1993 | Kuracina et al. | 604/198 |
| 5,256,152 A | 10/1993 | Marks | 604/198 |
| 5,256,153 A | 10/1993 | Hake | 604/198 |
| 5,277,311 A | 1/1994 | Hollister | 206/365 |
| 5,290,255 A | 3/1994 | Vallelunga et al. | 604/197 |
| 5,304,137 A | 4/1994 | Fluke | 604/110 |
| 5,312,369 A | 5/1994 | Arcusin et al. | 604/192 |
| 5,334,158 A | 8/1994 | McLees | 604/110 |
| 5,348,544 A | 9/1994 | Sweeney et al. | 604/192 |
| 5,356,392 A | 10/1994 | Firth et al. | 604/198 |

| | | | |
|---|---|---|---|
| 5,403,283 A | 4/1995 | Luther | 604/164 |
| 5,403,286 A | 4/1995 | Lockwood, Jr. | 604/110 |
| 5,407,436 A | 4/1995 | Toft et al. | 604/195 |
| 5,411,492 A | 5/1995 | Sturman et al. | 604/263 |
| 5,423,765 A | 6/1995 | Hollister | 604/192 |
| 5,423,766 A | 6/1995 | Di Cesare | 604/192 |
| 5,425,720 A | 6/1995 | Rogalsky et al. | 604/198 |
| 5,447,501 A | 9/1995 | Karlsson et al. | 604/198 |
| 5,466,223 A | 11/1995 | Bressler et al. | 604/110 |
| 5,480,385 A | 1/1996 | Thorne et al. | 604/110 |
| 5,487,733 A | 1/1996 | Caizza et al. | 604/110 |
| 5,487,734 A | 1/1996 | Thorne et al. | 604/195 |
| 5,490,841 A | 2/1996 | Landis | |
| 5,498,243 A | 3/1996 | Vallelunga et al. | 604/197 |
| 5,531,694 A | 7/1996 | Clemens et al. | 604/110 |
| 5,533,980 A | 7/1996 | Sweeney et al. | 604/192 |
| 5,538,508 A | 7/1996 | Steyn | 604/192 |
| 5,542,927 A | 8/1996 | Thorne et al. | 604/110 |
| 5,549,568 A | 8/1996 | Shields | 604/192 |
| 5,549,570 A | 8/1996 | Rogalsky | 604/198 |
| 5,549,708 A | 8/1996 | Thorne et al. | 604/110 |
| 5,562,629 A | 10/1996 | Haughton et al. | 604/158 |
| 5,562,631 A | 10/1996 | Bogert | 604/164 |
| 5,573,510 A | 11/1996 | Isaacson | 604/158 |
| 5,584,816 A | 12/1996 | Gyure et al. | 604/192 |
| 5,584,818 A | 12/1996 | Morrison | 604/197 |
| 5,599,318 A | 2/1997 | Sweeney et al. | 604/263 |
| 5,611,782 A | 3/1997 | Haedt | 604/198 |
| 5,643,220 A | 7/1997 | Cosme | 604/192 |
| 5,672,161 A | 9/1997 | Allen et al. | 604/198 |
| 5,695,474 A | 12/1997 | Daugherty | 604/162 |
| 5,695,477 A | 12/1997 | Sfikas | 604/241 |
| 5,700,249 A * | 12/1997 | Jenkins | 604/263 |
| 5,735,827 A | 4/1998 | Adwers et al. | 604/263 |
| 5,738,665 A | 4/1998 | Caizza et al. | 604/263 |
| 5,746,718 A | 5/1998 | Steyn | 604/192 |
| 5,746,726 A | 5/1998 | Sweeney et al. | 604/263 |
| 5,755,699 A | 5/1998 | Blecher et al. | 604/198 |
| 5,814,018 A | 9/1998 | Elson et al. | 604/110 |
| 5,817,064 A | 10/1998 | DeMarco et al. | 604/198 |
| 5,823,997 A | 10/1998 | Thorne | 604/110 |
| 5,843,041 A | 12/1998 | Hake et al. | 604/198 |
| 5,910,130 A | 6/1999 | Caizza et al. | 604/110 |
| 5,919,168 A | 7/1999 | Wheeler | 604/198 |
| 5,925,020 A | 7/1999 | Nestell | 604/198 |
| 5,951,522 A | 9/1999 | Rosato et al. | 604/177 |
| 5,957,892 A | 9/1999 | Thorne | 604/162 |
| 5,980,488 A * | 11/1999 | Thorne | 604/110 |
| 6,015,397 A | 1/2000 | Elson et al. | 604/192 |
| 6,036,675 A | 3/2000 | Thorne et al. | 604/232 |
| 6,149,629 A | 11/2000 | Wilson et al. | 604/198 |
| 6,171,284 B1 | 1/2001 | Kao et al. | 604/198 |
| RE37,110 E | 3/2001 | Hollister | 206/365 |
| 6,224,576 B1 | 5/2001 | Thorne et al. | 604/198 |
| RE37,252 E | 7/2001 | Hollister | 206/364 |
| 6,254,575 B1 | 7/2001 | Thorne, Jr. et al. | 604/198 |
| 6,280,420 B1 * | 8/2001 | Ferguson et al. | 604/198 |
| 6,334,857 B1 | 1/2002 | Hollister et al. | 604/263 |
| 6,582,397 B1 | 6/2003 | Alesi et al. | 604/110 |
| 2001/0039401 A1 | 11/2001 | Ferguson et al. | |
| 2002/0004650 A1 | 1/2002 | Kuracine et al. | |
| 2002/0072716 A1* | 6/2002 | Barrus et al. | 604/192 |
| 2003/0004465 A1 | 1/2003 | Ferguson et al. | |
| 2003/0088215 A1* | 5/2003 | Ferguson et al. | 604/198 |
| 2003/0229317 A1* | 12/2003 | Ferguson et al. | 604/263 |

FOREIGN PATENT DOCUMENTS

| | | |
|---|---|---|
| EP | 0 344 606 A2 | 12/1989 |
| EP | 0 457 477 B1 | 11/1991 |
| EP | 0 485 345 B1 | 5/1992 |
| EP | 0 533 308 A1 | 3/1993 |
| EP | 0 585 391 B1 | 3/1994 |
| EP | 0 597 857 B1 | 5/1994 |
| EP | 0 603 365 B1 | 6/1994 |
| EP | 0 626 924 B1 | 12/1994 |
| EP | 0 654 281 B1 | 5/1995 |
| EP | 0 705 613 B1 | 4/1996 |
| EP | 0 713 710 A1 | 5/1996 |
| EP | 0 807 443 A2 | 11/1997 |
| EP | 0 815 888 A2 | 1/1998 |
| EP | 0 815 890 A2 | 1/1998 |
| EP | 0 819 441 A1 | 1/1998 |
| EP | 0 832 659 A2 | 4/1998 |
| EP | 0 832 660 A2 | 4/1998 |
| EP | 1 092 443 A2 | 4/2001 |
| EP | 1 116 493 A1 | 7/2001 |
| GB | 1233302 | 5/1971 |
| GB | 2 283 429 A | 5/1995 |
| GB | 2 369 779 | 6/2002 |
| JP | 10-76007 | 3/1998 |
| JP | 10-127765 | 5/1998 |
| WO | WO 87/07162 | 12/1987 |
| WO | WO 89/07955 | 9/1989 |
| WO | WO 93/17732 | 9/1993 |
| WO | WO 94/19036 | 9/1994 |
| WO | WO 97/31666 | 9/1997 |
| WO | WO 98/07463 | 2/1998 |
| WO | WO 98/10816 | 3/1998 |
| WO | WO 98/11928 | 3/1998 |
| WO | WO 98/13081 | 4/1998 |
| WO | WO 00/16832 | 3/2000 |
| WO | WO 00/38765 | 7/2000 |
| WO | WO 01/32241 A1 | 5/2001 |
| WO | WO 01/32244 A1 | 5/2001 |

* cited by examiner

SAFETY SHIELD FOR MEDICAL NEEDLES

CROSS-REFERENCE TO RELATED APPLICATIONS

This patent application is a continuation-in-part of U.S. Utility patent application Ser. No. 09/892,593, filed in the U.S. Patent and Trademark Office on Jun. 27, 2001 by Ferguson et al., the entire contents of which being hereby incorporated by reference herein, application Ser. No. 09/892,593 is a continuation-in-part of U.S. Utility patent application Ser. No. 09/433,449, filed Nov. 4, 1999, now U.S. Pat. No. 6,280,420; application Ser. No. 09/892,593 is also a continuation-in-part of U.S. patent application Ser. No. 09/434,036, filed Nov. 4, 1999, now U.S. Pat. No. 6,254,575; and application Ser. No. 09/892,593 is also a continuation-in-part of U.S. patent application Ser. No. 09/619,190, filed Jul. 19, 2000, now U.S. Pat. No. 6,592,556; application Ser. No. 09/892,593 claims the benefit of U.S. Provisional Patent Application Ser. No. 60/254,506, filed on Dec. 8, 2000; application Ser. No. 09/892,593 also claims the benefit of U.S. Provisional Patent Application Ser. No. 60/275,810, filed on Mar. 14, 2001; application Ser. No. 09/892,593 also claims the benefit of U.S. Provisional Patent Application Ser. No. 60/275,886, filed Mar. 14, 2001; and application Ser. No. 09/892,593 also claims the benefit of U.S. Provisional Patent Application Ser. No. 60/296,968, filed Jun. 8, 2001.

BACKGROUND

1. Technical Field

The present disclosure generally relates to safety shields for medical needles, and more particularly, to safety shields that are extensible to prevent hazardous exposure to a needle.

2. Description of the Related Art

Problems associated with inadvertent needle sticks are well known in the art of blood sampling, percutaneous medication injection and other medical procedures involving use of medical needles. Significant attention has been focused on needle stick problems due to the contemporary sensitivity of exposure to AIDS, Hepatitis and other serious blood-borne pathogen exposures.

Procedures for removing a needle from a patient commonly require a clinician to use one hand to place pressure at the wound site where a needle is being withdrawn, while removing the needle device with the other hand. It is also common practice for a clinician to give higher priority to care for the wound than is given to disposal of the needle. In the case of typical needle devices without safety shields, such priority either requires the convenience of an available sharps container within reach or another means for safe disposal, without leaving the patient's side. Thus, the difficulty in providing adequate care while following safety procedures is often compounded by the patient's physical condition and mental state, such as in burn units and psychiatric wards. Under such conditions, proper disposal of a used needle, while caring for a patient, is a technological challenge to the state of the art.

The widespread knowledge and history associated with needle care and disposal problems have resulted in numerous devices for preventing accidental needle sticks. Some devices utilize a separate sheath or cap mounted over the needle after use. These devices, however, require two handed manipulation from a practitioner.

Other known devices employ sheaths that are spring activated, telescoping, pivoting, etc. These devices, however, may disadvantageously misfire or be cumbersome to activate. Further drawbacks of current devices include high manufacturing cost due to complexity and the number of parts. Thus, these type prior art devices may not adequately and reliably shield needle infusion and/or fluid collection apparatus to prevent hazardous exposure.

Consequently, there remains a need to provide a more satisfactory solution for needle safety devices by overcoming the disadvantages and drawbacks of the prior art. Therefore, it would be desirable to provide a more adequate and reliable medical needle shield apparatus which employs an extensible safety shield to prevent hazardous exposure to a needle. Such a needle shield apparatus should be easily and reliably extendable to shield a needle tip of a needle cannula. It would be desirable if the needle shield apparatus was actuated via one handed operation. It would be highly desirable if the medical needle shield apparatus facilitates efficient assembly and manufacture thereof.

SUMMARY

Accordingly, the present disclosure addresses a need for a medical needle shield apparatus which effectively and inexpensively protects a medical needle of a syringe and/or fluid collection device after use. The present disclosure resolves related disadvantages and drawbacks experienced in the art. More specifically, the apparatus and method of this invention constitute an important advance in the art of safety needle devices.

In one particular embodiment, a prefilled medical needle shield apparatus is provided in accordance with the principles of the present disclosure. The prefilled medical needle shield apparatus includes a collar and hingedly connected segments extensible from the collar. The shield is extensible from a retracted position to an extended position. The collar is configured to attach to a distal end of a prefilled syringe.

The shield may be locked in the extended position. The shield may also be irreversibly locked in the extended position. The shield may be locked in the extended position via engagement with the needle. The lock may include a portion configured to flexibly engage the needle and bias to lockably retain the needle. Alternatively, the shield includes locking means to lock the shield in the extended position. In another embodiment, the distal end of the shield includes a surface configured to enclose at least a portion of the distal end of the needle. The distal end of the shield may have a surface configured to align the shield with the needle.

In another embodiment, the shield includes a catch that engages a corresponding latch to releasably dispose the shield in the retracted position. In another alternate embodiment, the shield has a manipulating actuator configured to urge the shield towards the extended position. The shield segments may be connected via living hinges. The shield may include a needle flap lock that engages the needle in the extended position.

In another embodiment, the distal segment has an underside including a surface extending over at least a portion of the distal segment for retaining the distal end of the needle. The shield may include at least one flap lock associated with the distal segment and/or proximal segment for securing the shield in the extended position. The medical needle shield apparatus may include a retainer for holding the segments in a retracted position. The retainer can include a retainer arm disposed on the needle hub and extending to a corresponding catch disposed on the shield in the retracted position.

In another embodiment, at least one segment includes at least one needle guide for facilitating extension of the segments when extending the shield over the needle. The shield may further include a raised surface for aid in urging the shield to the extended position.

In another particular embodiment, in accordance with the principles of the present disclosure, the medical needle shield apparatus includes an extensible shield having a first segment and a second segment extending therefrom. The second segment includes an opening configured for clearance of a medical needle of a medical needle device during attachment of the extensible shield to the medical needle device. The second segment defines a planar surface adjacent a distal portion thereof. The planar surface is configured to engage the needle for disposing the shield in an extended position. In another alternate embodiment, the second segment has extending means for facilitating extension of the shield from a retracted position to an extended position about a needle.

In yet another alternate embodiment, the medical needle shield apparatus has a syringe having a needle hub supporting a needle. An extensible shield includes a first segment and a second segment articulating therefrom. The first segment articulates from a collar disposed about the needle hub. The collar includes a pair of latches. The opening is configured for travel about the needle to facilitate extension of the shield from a retracted position to an extended position. The second segment further includes a proximal fulcrum that engages the needle to facilitate extension of the shield. The second segment also has a pair of catches. The catches are engageable with the latches to maintain the shield in the retracted position. The second segment has a nose portion defining a planar surface configured to engage the needle to facilitate fixing the shield in the extended position.

A method of assembling a medical needle shield with a medical needle device is disclosed, in accordance with the principles of the present disclosure. The method includes the steps of: providing a medical needle device having a medical needle extending therefrom; providing a medical needle shield including: an extensible shield including a first segment and a second segment extending therefrom, the second segment including an opening configured for clearance of the medical needle during attachment of the medical needle shield to the medical needle device, the opening being transversely oriented relative to the distal segment; positioning the medical needle shield for assembly with the medical needle device such that the needle travels through the opening and the first segment is disposed for mounting with the medical needle device; and mounting the first segment to the medical needle device.

The step of providing a medical needle shield may further include the proximal segment being articulated to a collar and the step of mounting further including mounting the first segment to the medical needle device by attaching the collar to an outer surface of the medical needle device.

The step of providing a medical needle shield may include a circumferential wall of the second segment which defines the opening. Alternatively, the step of providing a medical needle device further includes a needle cover mounted to the medical needle device and substantially enclosing the medical needle and the step of manipulation further includes manipulation such that the needle cover travels through the opening.

BRIEF DESCRIPTION OF THE DRAWINGS

The foregoing and other features and advantages of the present disclosure will be more fully understood from the following detailed description of the exemplary embodiments, taken in conjunction with the accompanying drawings in which.

DETAILED DESCRIPTION OF THE EXEMPLARY EMBODIMENTS

The exemplary embodiments of the medical needle shield apparatus and methods of operation disclosed are discussed in terms of medical needles for infusion of intravenous fluids, medication infusion or fluid collection, and more particularly, in terms of needle shield apparatus employed with a needle cannula that prevent hazardous exposure to the needle cannula, including, for example, inadvertent needle stick. It is contemplated that the needle cannula may be shielded during use including storage, transport, fluid infusion and/or collection, subsequent thereto, etc. It is envisioned that the present disclosure, however, finds application to a wide variety of cannula needles and devices for the infusion of preventive medications, medicaments, therapeutics, etc. to a subject. It is also envisioned that the present disclosure may be employed for collection of body fluids including those employed during procedures relating to phlebotomy, digestive, intestinal, urinary, veterinary, etc. It is contemplated that the medical needle shield apparatus may be utilized with other medical needle applications including phlebotomy devices, catheters, catheter introducers, guide wire introducers, spinal and epidural, biopsy, aphaeresis, dialysis, blood donor, Veress needles, Huber needles, etc.

In the discussion that follows, the term "proximal" refers to a portion of a structure that is closer to a clinician, and the term "distal" refers to a portion that is further from the clinician. As used herein, the term "subject" refers to a patient that receives infusions or has blood and/or fluid collected therefrom using the medical needle shield apparatus. According to the present disclosure, the term "clinician" refers to an individual administering an infusion, performing fluid collection, installing or removing a needle cannula from a medical needle shield apparatus and may include support personnel.

The following discussion includes a description of the medical needle shield apparatus, followed by a description of the method of operating the medical needle shield apparatus in accordance with the present disclosure. Reference will now be made in detail to the exemplary embodiments of the disclosure, which are illustrated in the accompanying figures.

Turning now to the figures, wherein like components are designated by like reference numerals throughout the several views. Referring initially to FIGS. 1–8, there is illustrated a medical needle shield apparatus including an extensible shield, such as, for example, safety shield 10, constructed in accordance with the principals of the present disclosure. Safety shield 10 is advantageously configured to prevent hazardous exposure to a needle cannula 15 by providing an adequate and reliable medical needle shield apparatus for a needle infusion and/or fluid collection device which shields a needle via one handed operation, as will be discussed below.

Safety shield 10 is attached to a medical needle device, such as, for example, prefilled syringe 11 to facilitate safe infusion of fluids to a subject (not shown) from a sterile cartridge or the like. Safety shield 10 may be attached to prefilled syringe 11 via spin welding, adhesive, other welding methods, etc. Alternatively, safety shield 10 may be monolithically, integrally connected, etc. with the distal end of prefilled syringe 11. Safety shield 10 is employed with a needle cannula 15 supported by a needle hub 50 of prefilled syringe 11. It is contemplated that a syringe employed may be prefilled with a fluid, such as a pharmaceutical medication or may be a prefillable syringe which is subsequently filled with a medication. It is further contemplated that safety shield 10 may be used with other fluid infusion, fluid collection, catheters, introducers, etc., similar to those described above.

Safety shield 10 includes a first segment, such as, for example, proximal segment 14 and a second segment, such as, for example, distal segment 16 extending therefrom. Distal segment 16 includes a circumferential wall, such as, for example, a cylinder 24. Cylinder 24 is disposed about needle cannula 15 and configured to facilitate extension of safety shield 10 between a retracted position (FIG. 1) and an extended position (FIG. 5), as will be discussed.

Distal segment 16 defines a planar surface, such as, for example, a base 32, discussed in more detail below, adjacent a distal portion 52 thereof. Base 32 is configured to engage needle cannula 15 for disposing safety shield 10 in the extended position.

Thus, another advantage of the present disclosure is that safety shield 10 is easily extendable via one handed activation, resulting in a higher degree of safety to the clinician and subject. Further, this configuration of safety shield 10 advantageously provides guided extension of the shield to reliably prevent hazardous exposure to needle cannula 15 during manipulation.

Safety shield 10 is desirably contemplated for use in the field of medical fluid infusion and/or collection. More particularly, safety shield apparatus 10 is envisioned to be a disposable needle device employing, among other things, safety features having shielding capabilities to prevent inadvertent sticking or punctures of clinicians and subjects, as well as uniform and dependable movement during a procedure and a locking mechanism for reliable use. The above advantages, among others, realized from the present disclosure are attained through the disclosed safety shield 10, which is extensible to a protective configuration, as discussed hereinbelow. These features of the present disclosure advantageously facilitate a safe infusion and/or collection of fluids and prevent inadvertent needle stick of a clinician and subject.

Safety shield 10 is monolithically formed. It is contemplated, however, that the component parts of safety shield 10 may be integrally assembled. Safety shield 10 can be fabricated from a material suitable for medical applications, such as, for example, polymerics or metals, such as stainless steel, depending on the particular medical application and/or preference of a clinician. Semi-rigid and rigid polymerics are contemplated for fabrication, as well as resilient materials, such as molded medical grade polypropylene. However, one skilled in the art will realize that other materials and fabrication methods suitable for assembly and manufacture, in accordance with the present disclosure, also would be appropriate. Alternatively, portions of safety shield 10 can be monolithically formed and assembled therewith.

Proximal segment 14 is articulated to a collar 12 via a hinged connection. It is contemplated that the hinged connection of proximal segment 14 to collar 12 may be living hinges, pinned hinges, etc., or alternatively, may be movably connected by other structure, such as, ball joint, etc. As shown in FIGS. 5–8, a pair of arms 54 extend to collar 12 and connect thereto via living hinges 19. This configuration provides movement of proximal segment 14 relative to collar 12, facilitating extension of safety shield 10. It is envisioned that one or a plurality of hinged connections may be used. Collar 12 is fixedly mounted to an outer surface of a distal end of prefilled syringe 11, such as, for example, a luer lock collar 38. Luer lock collar 38 is disposed about needle hub 50. Collar 12 may also be mounted directly to needle hub 50 or various portions of prefilled syringe 11.

Figure 1:
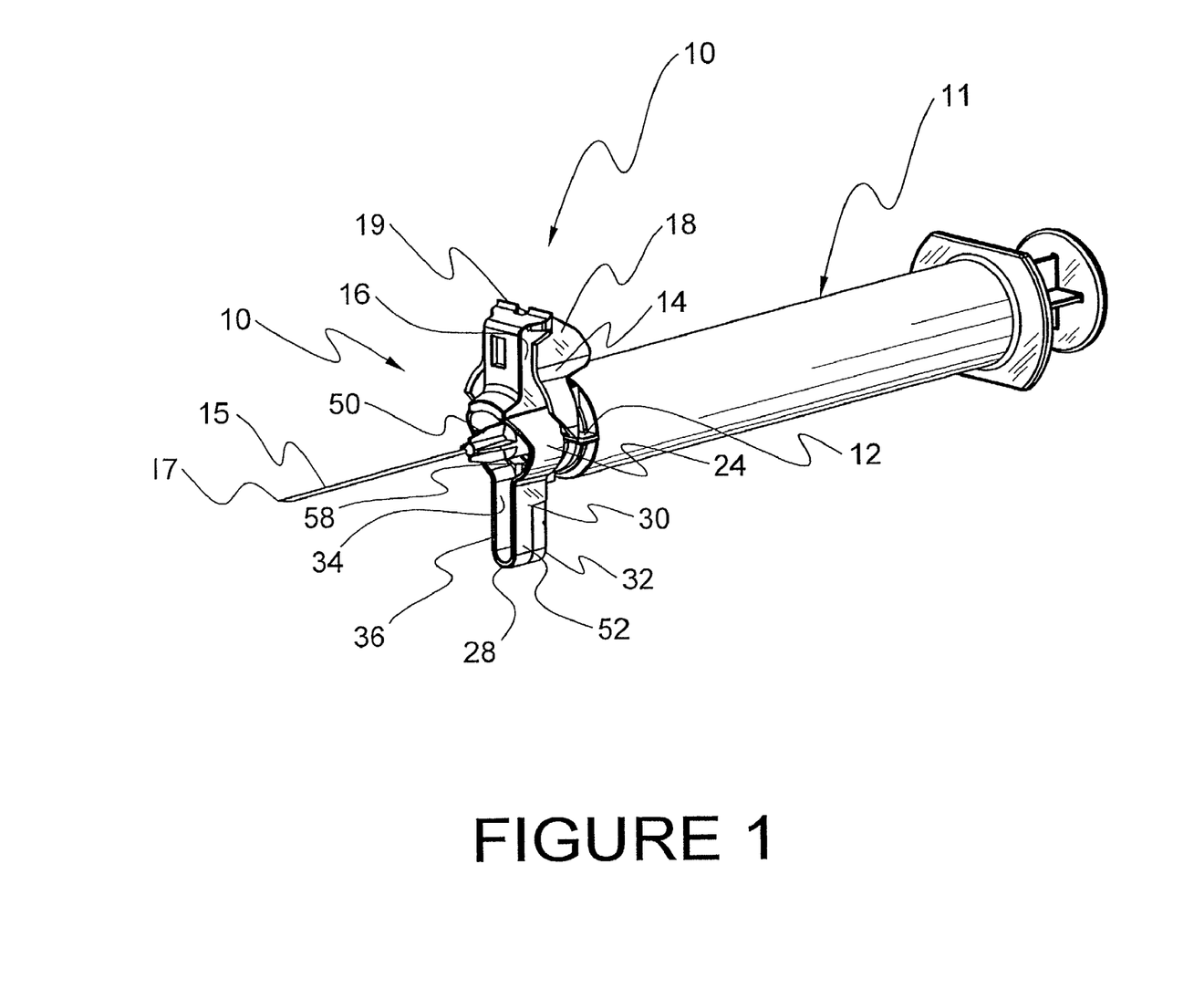
FIG. 1 is a perspective view of a medical needle safety shield apparatus in accordance with the principles of the present disclosure.
Figure 2:
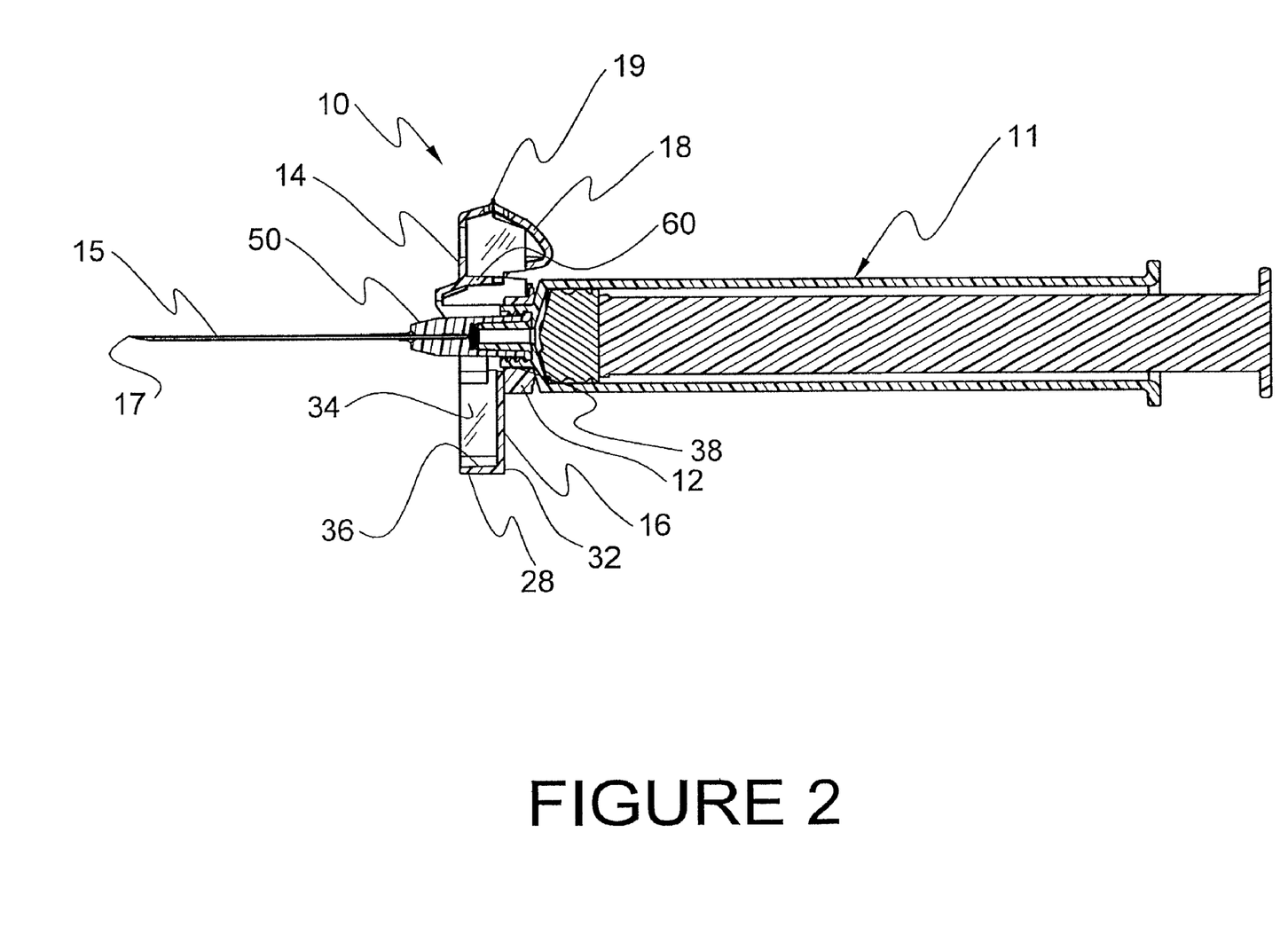
FIG. 2 is a cross-sectional view of the safety shield apparatus shown in FIG. 1.
Figure 3:
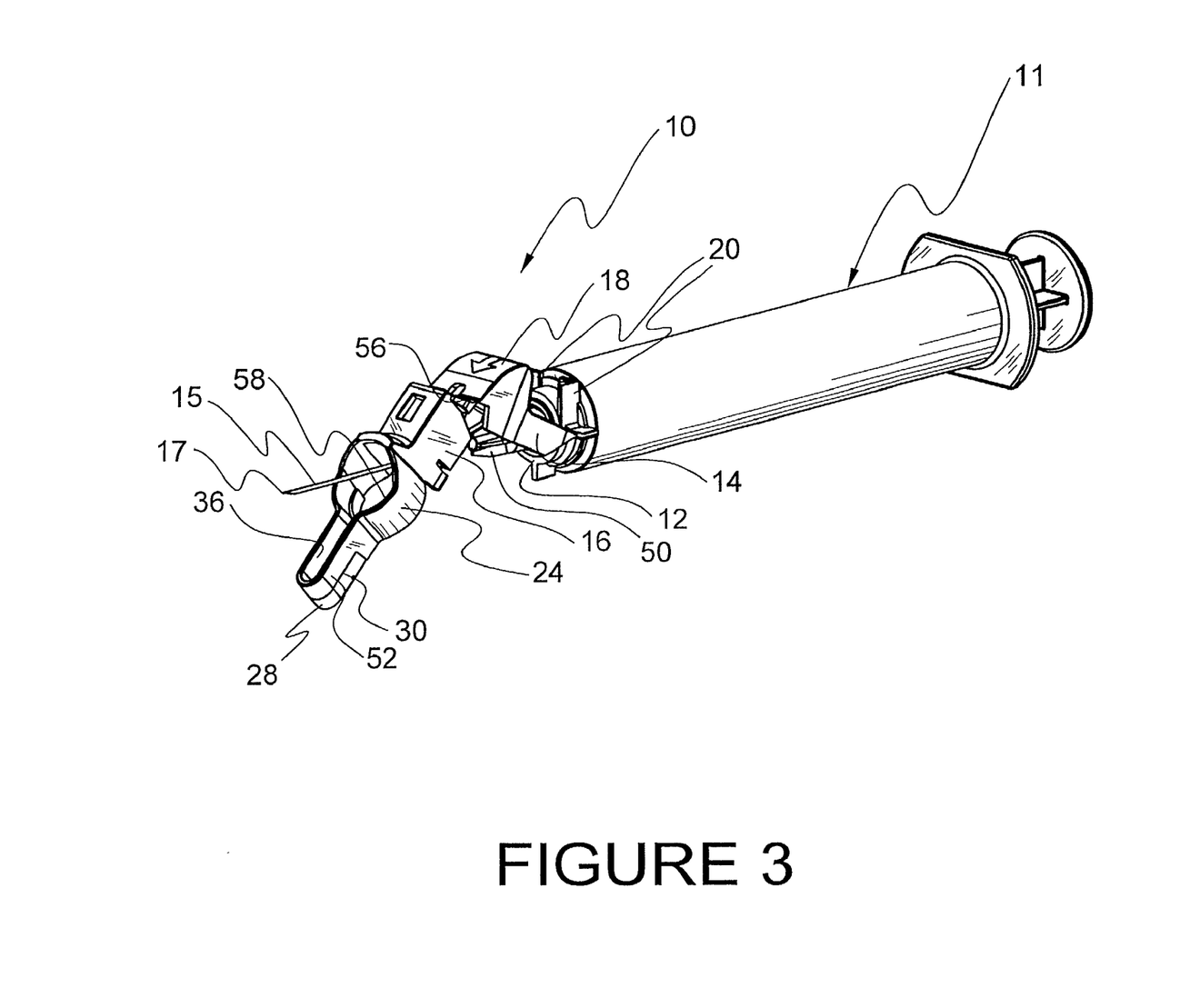
FIG. 3 is a perspective view of the safety shield apparatus shown in FIG. 1 during extension.
Figure 4:
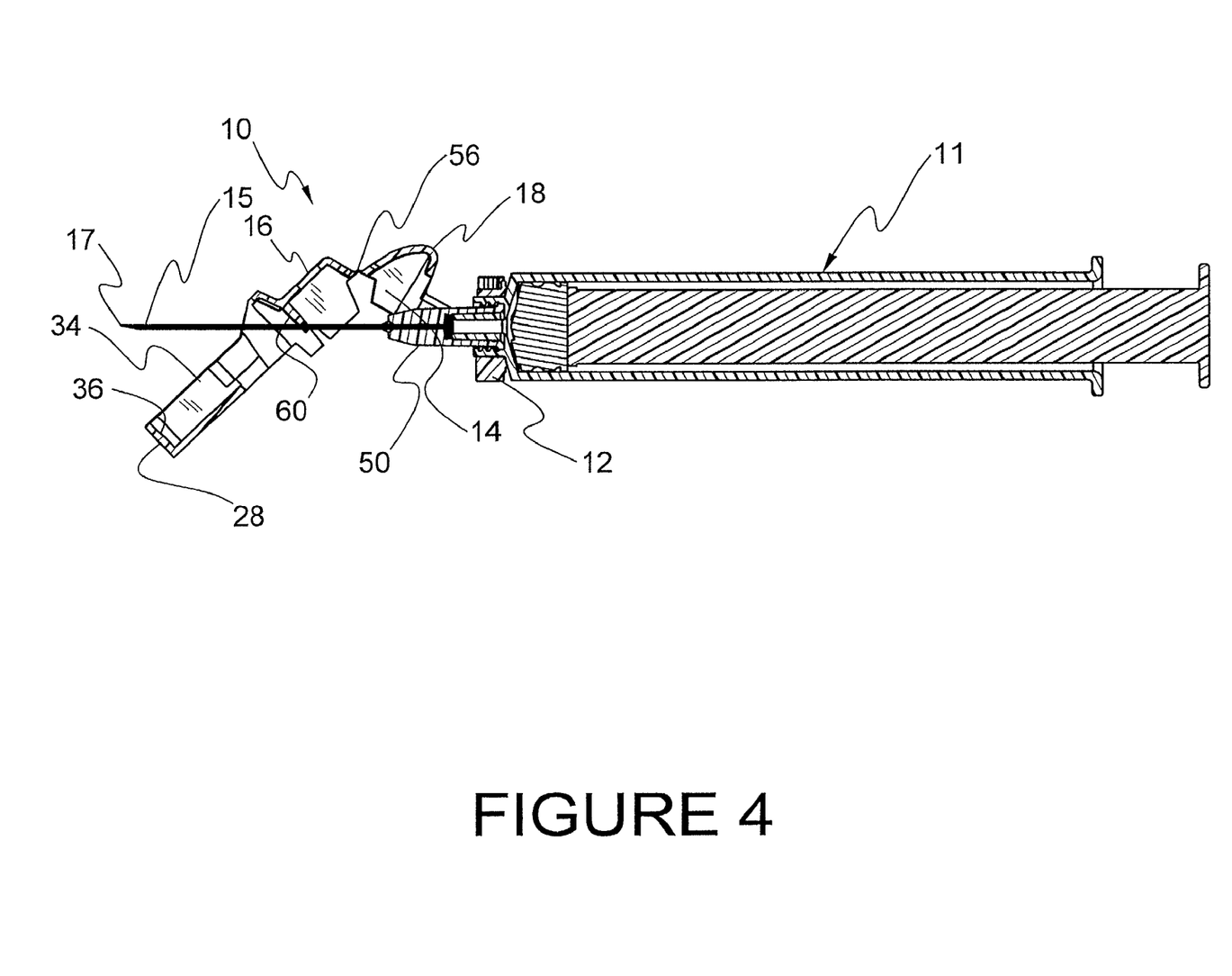
FIG. 4 is a cross-sectional view of the safety shield apparatus shown in FIG. 3.
Figure 5:
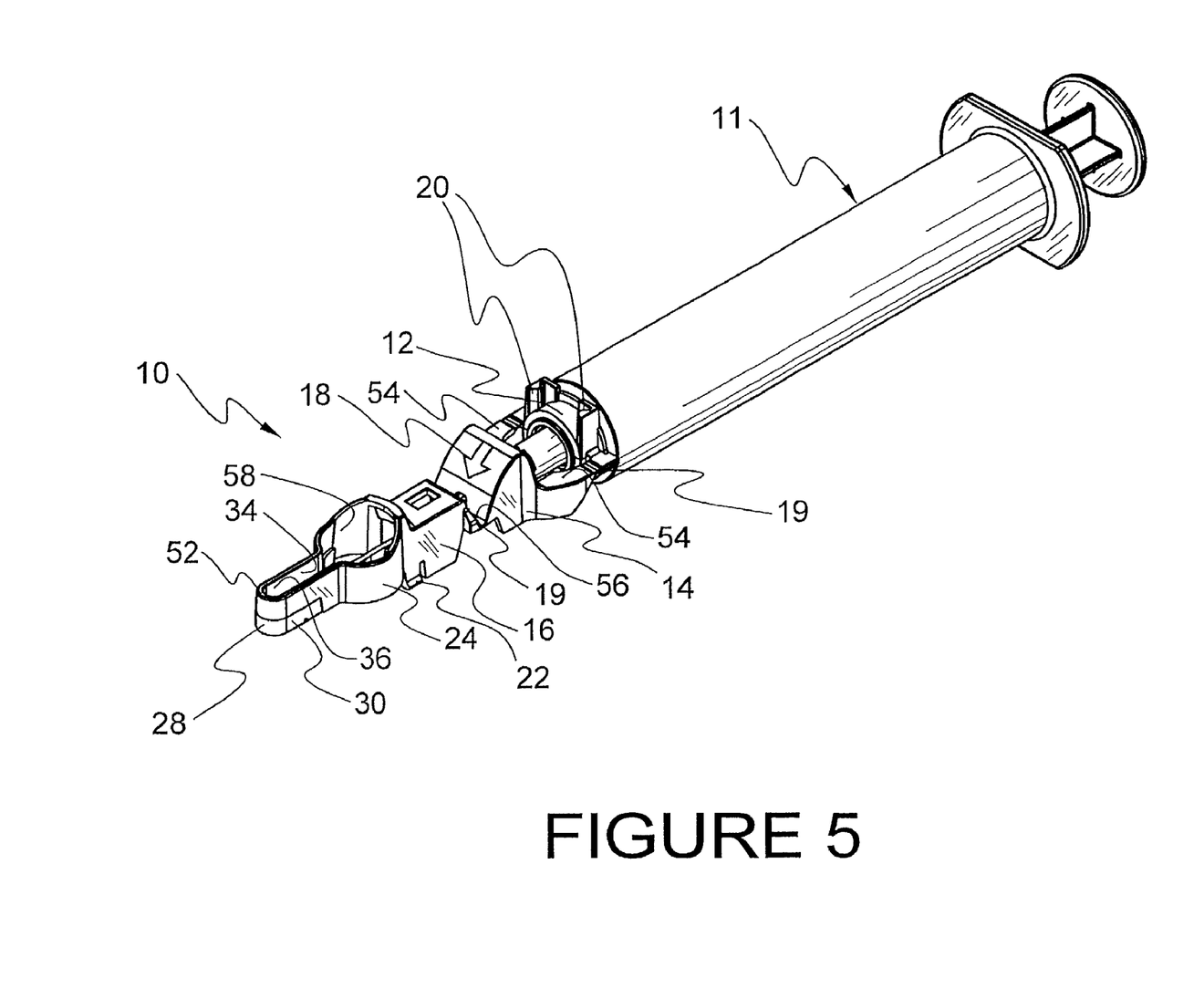
FIG. 5 is a perspective view of the safety shield apparatus shown in FIG. 1 in the extended position.
Figure 6:
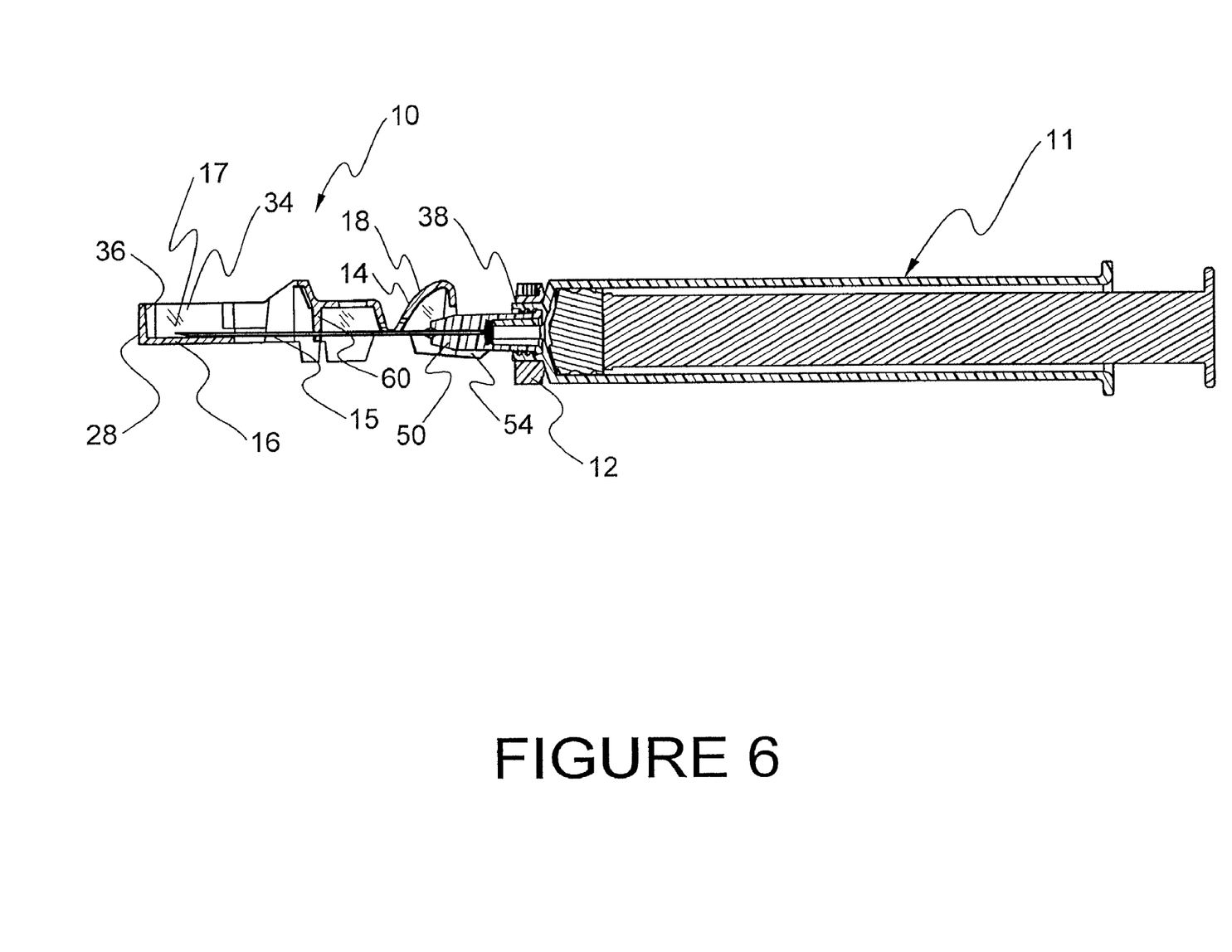
FIG. 6 is a cross-sectional view of the safety shield apparatus shown in FIG. 4.
Figure 7:
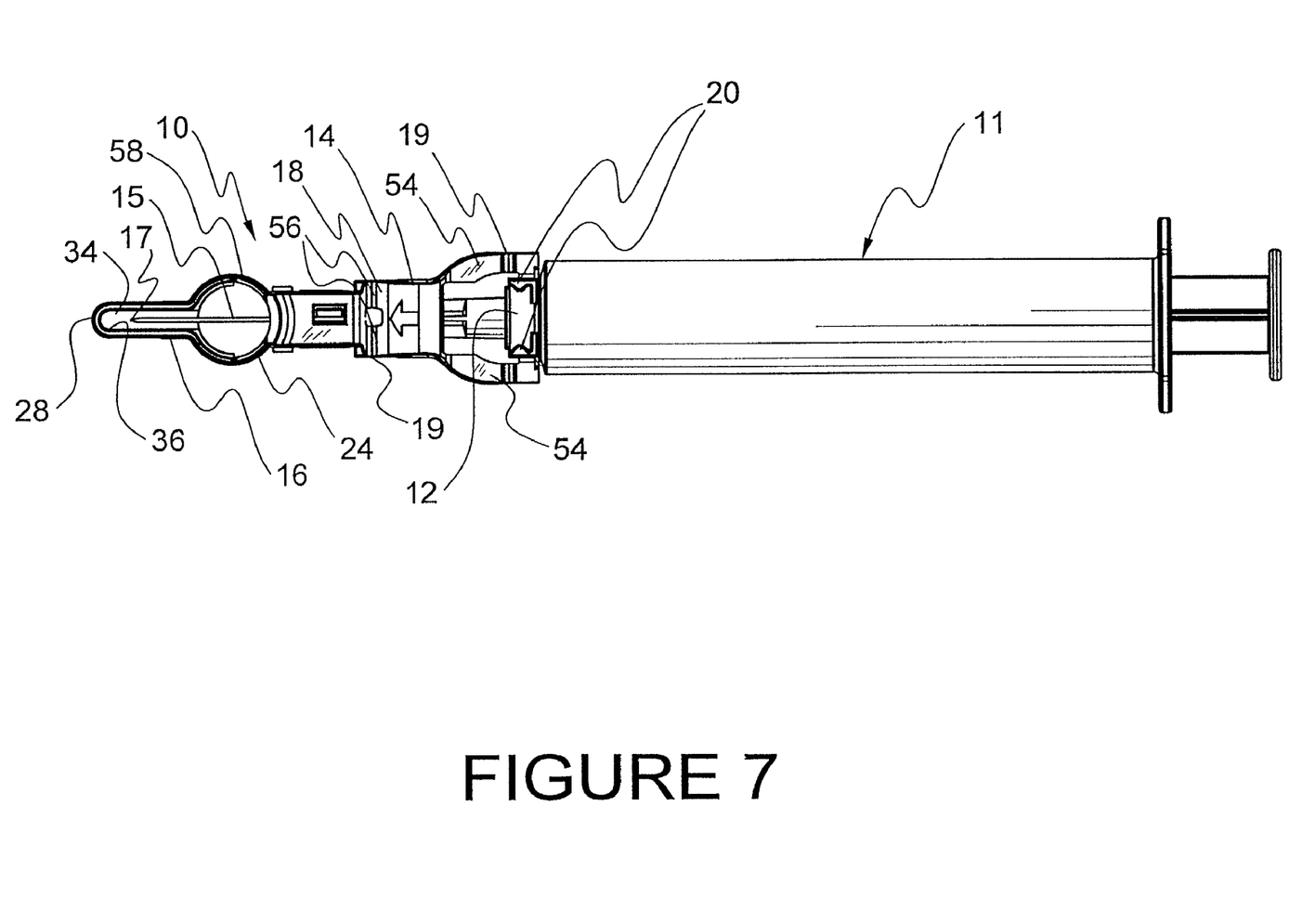
FIG. 7 is a top view of the safety shield apparatus shown in FIG. 5.

Referring to FIGS. 1, 2 and 5, collar 12 includes a pair of latches 20 disposed for engagement with a corresponding pair of catches 22 formed with distal segment 16. Cooperative engagement of latches 20 and catches 22 releasably locks safety shield 10 in the retracted position. Latches 20 have a female-type configuration for releasably receiving catches 22 male-type component part in a snap fit engagement. The releasable locking engagement provides a tactile feel and audible signal that safety shield 10 is in the retracted position.

To release safety shield 10 from the retracted position, a manual actuator 18 provides an engagement surface for urging safety shield 10 to the extended position and consequently disengaging catches 22 from latches 20. It is envisioned that other releasable engagements may be employed such as, for example, friction fit, interference fit, etc., that the male/female components are reversed, or, alternatively that no such releasable engagement is used.

Distal segment 16 articulates from proximal segment 14 in a hinged connection. It is contemplated that the hinged connection of proximal segment 14 and distal segment 16 may be living hinges, pinned hinges, etc., or alternatively, may be movably connected by other structure, such as ball joint, etc. A pair of arms 56 extend from proximal segment 14 to distal segment 16 for corresponding connection via living hinges 19. This configuration provides movement of distal segment 16 relative to proximal segment 14 facilitating extension of safety shield 10. It is envisioned that one or a plurality of hinged connections may be used. Upon engagement of manual actuator 18 with a clinician's hand, finger, etc., or a table top, etc., safety shield 10 is urged from the retracted position to the extended position for protecting a sharpened tip 17 of needle cannula 15 after a medical procedure.

Distal segment 16 includes cylinder 24 which defines an opening 58. Opening 58 is transversely oriented relative to the body of distal segment 16. Opening 58 is configured such that cylinder 24 travels about needle cannula 15 to facilitate extension of safety shield 10. Cylinder 24 and opening 58 provide a cavity to accommodate needle cannula 15 such that segments 14, 16 uniformly extend from the retracted position to the extended position via one handed operation. This configuration advantageously maintains safety shield 10 in alignment with needle cannula 15 during extension thereof. It is contemplated that cylinder 24 may have alternative configurations, such as, for example, rectangular, elliptical, polygonal, etc., or cylinder 24 may have various dimensions, according to the requirements of a particular medical needle application.

Figure 8:
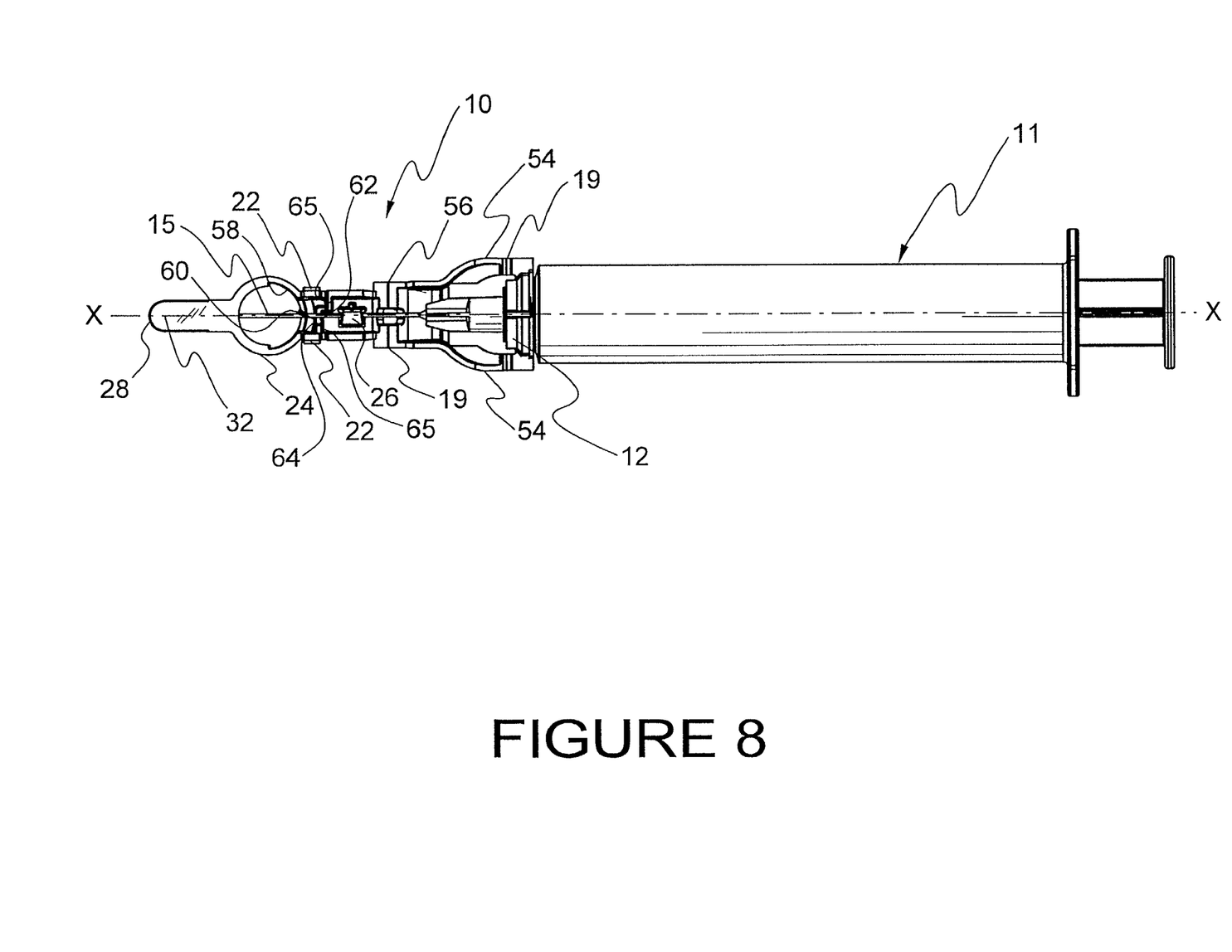
FIG. 8 is a bottom view of the safety shield apparatus shown in FIG. 5.
Figure 8A:
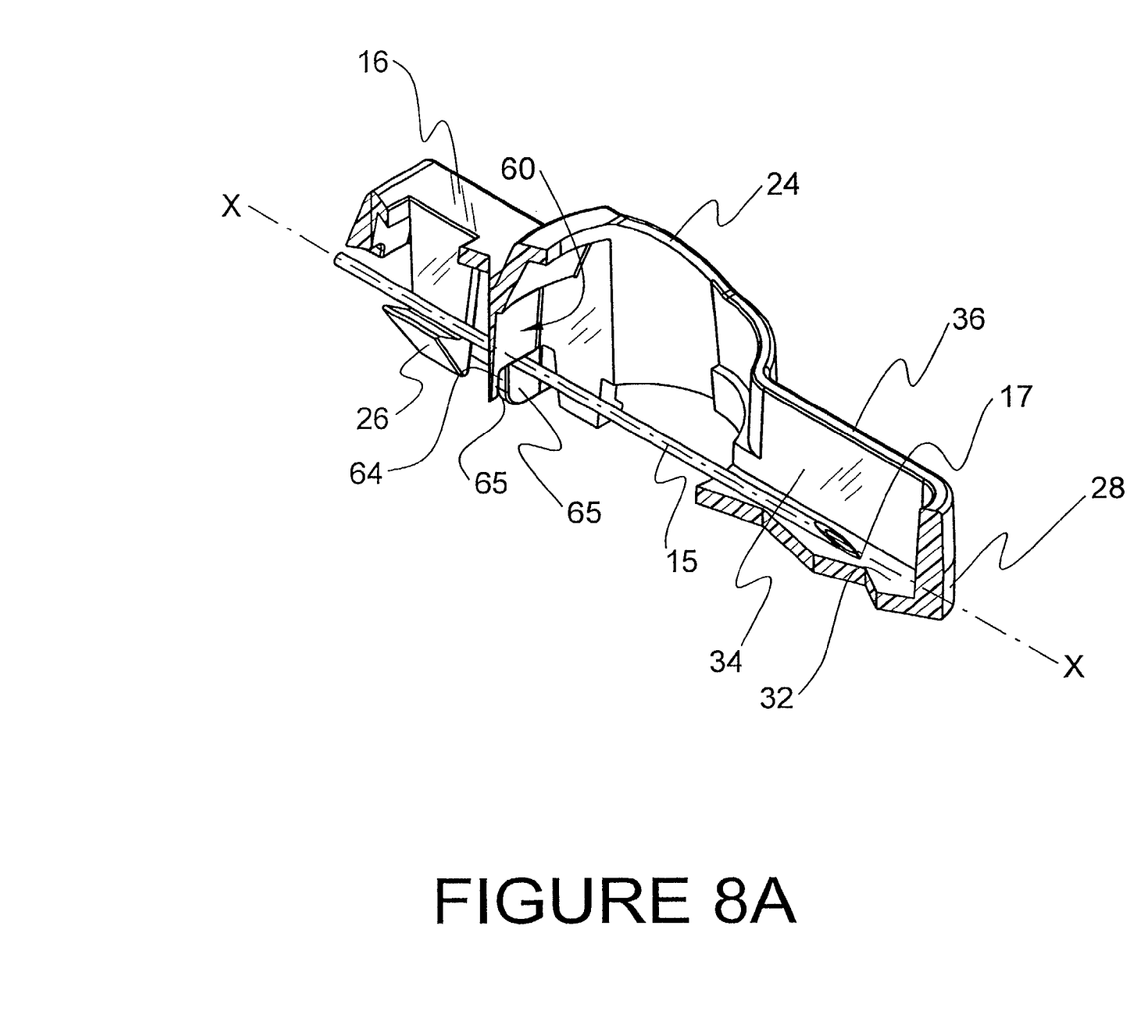
FIG. 8A is a cutaway perspective view of the safety shield apparatus shown in FIG. 1.

Distal segment 16 includes a fulcrum 60, as shown in FIGS. 8 and 8A, disposed adjacent a proximal portion thereof to facilitate extension of safety shield 10. Fulcrum 60 is configured to engage needle cannula 15 to facilitate extension of segments 14, 16 from the retracted position to the extended position. Fulcrum 60 includes a slot 62 configured to guide needle cannula 15 therein during extension of safety shield 10. Slot 62 defines an opening with walls 64, 65 which receive needle cannula 15 to maintain safety shield 10 in alignment therewith. Walls 64, 65 are oriented in a plane substantially transverse to longitudinal axis x. Wall 64 is oriented substantially orthogonal to walls 65. It is envisioned that walls 64, 65 may be at various angular orientations relative to longitudinal axis x. It is further envisioned that walls 64, 65 may be disposed at various angular orientations relative to each other.

Needle cannula 15 engages wall 64 and wall 65 which serve as a fulcrum and a guide to extend safety shield 10 into alignment with longitudinal axis x of needle cannula 15. The resistive forces created via engagement of wall 64 and needle cannula 15, and continued manipulation of manipulable actuator 18 force such extension of segments 14, 16. This configuration facilitates extension of safety shield 10 via one handed operation. It is contemplated that slot 62 may have other configurations such as, for example, arcuate walls 64, 65, etc., or alternatively, may define a larger or smaller opening, according to the requirements of a particular medical needle application. It is further contemplated that needle cannula 15 may engage only wall 64 or walls 65.

A nose portion 28 of distal segment 16 projects from opening 58 of cylinder 24 and is in communication therewith via channel 36. Nose portion 28 includes side walls 30 and base 32 that define a cavity 34. Cavity 34 is configured for disposal of needle cannula 15 when safety shield 10 is in the extended position. Base 32 extends from cylinder 24 to the distal end of nose portion 28. Channel 36 connects opening 58 and cavity 34 facilitating extension of safety shield 10.

As segments 14, 16 extend about needle cannula 15, cylinder 24 travels about needle cannula 15. Needle cannula 15 is caused to travel through cavity 34. As safety shield 10 approaches the extended position, needle cannula 15 engages base 32. Base 32 forces segments 14, 16 to further extend and align with needle cannula 15 along longitudinal axis x thereof to dispose safety shield 10 in the extended position. In this position, needle cannula 15 is protectively shielded by nose portion 28 and safety shield 10 is disposed in the extended position. Safety shield 10 thereby prevents hazardous exposure to needle cannula 15 and needle tip 17 thereof. This configuration advantageously protects a clinician and subject from accidental needlestick via one handed operation of safety shield 10. Base 32 may cover all or a portion of the underside surface of nose portion 28.

Figure 11:
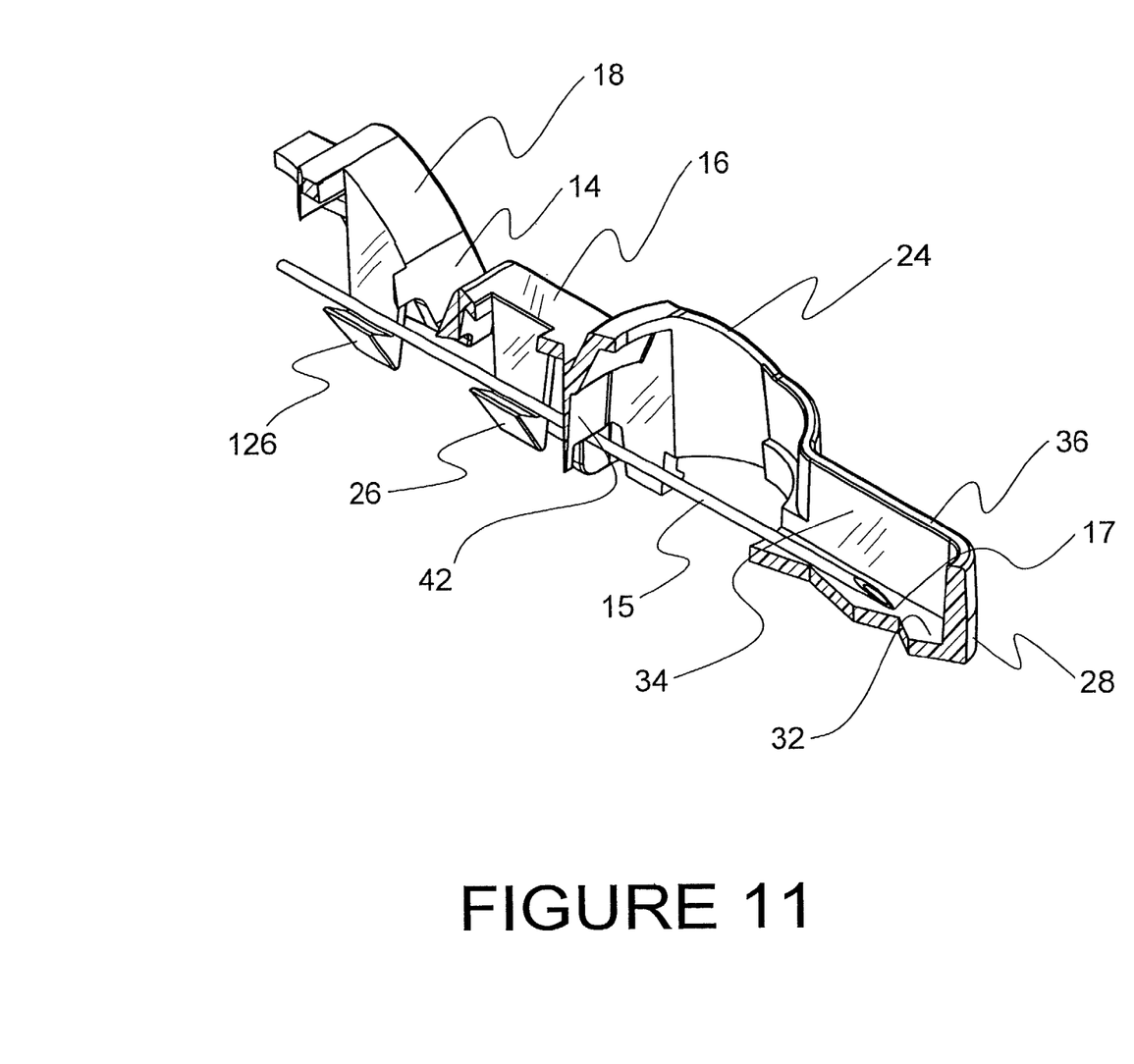
FIG. 11 is a cutaway perspective view of an alternate embodiment of a locking arrangement for the safety shield apparatus shown in FIG. 1.

Distal segment 16 includes a barbed flap lock 26 that engages needle cannula 15 to fix safety shield 10 in the extend position. As safety shield 10 approaches the extended position, needle cannula 15 engages base 32. Needle cannula 15 is thereby caused to engage lock 26 whereby lock 26 deflects about needle cannula 15. Continued manipulation of safety shield 10, via manual actuator 18, and corresponding engagement of needle cannula 15 and base 32, causes needle cannula 15 to travel over a barbed portion of lock 26 and come to rest on an opposite side thereof. Lock 26 returns to an undeflected position to non-releasably fix safety shield 10 in the extended position. This provides an added degree of security to the clinician and subject from accidental needle stick. Alternatively, as shown in FIG. 11, proximal segment 14 has a barbed flap lock 126, similar to lock 26, formed on an inner surface thereof. Lock 126, either alone or in cooperation with lock 26, non-releasably fixes safety shield 10 in the extended position. Other lock configurations are also envisioned.

In preparation for use of a medical needle shield apparatus, similar to that described above, a medical needle shield, such as, for example, safety shield 10 is assembled with a medical needle device, such as, for example, prefilled syringe 11. The method of assembly includes the steps of providing prefilled syringe 11 and safety shield 10. Needle cannula 15 extends from prefilled syringe 11. A needle cover 40 is mounted to prefilled syringe 11 and substantially encloses needle cannula 15. Opening 58 of safety shield 10 is configured for clearance of needle cannula 15 during attachment of safety shield 10 with prefilled syringe 11. As discussed above, opening 58 is transversely oriented relative to distal segment 16. It is envisioned that safety shield 10 is provided for assembly with prefilled syringe 11 at the end of a manufacturing process for syringe 11. Others arrangements are contemplated such as introducing safety shield 10 at various stages of manufacture of syringe 11.

Safety shield 10 is positioned for assembly with prefilled syringe 11 such that needle cover 40 (FIGS. 9 and 10) and needle cannula 15, substantially enclosed therein, travel through opening 58. It is contemplated that the component parts of the medical needle shield apparatus may be manipulated for assembly by personnel, mechanical devices, etc. It is further contemplated that the inner surface of cylinder 24 may or may not engage needle cover 40 during positioning. Prefilled syringe 11 may or may not include the needle cover.

Proximal segment 14 is disposed for mounting with prefilled syringe 11. As discussed, proximal segment 14 includes collar 12. Proximal segment 14 is mounted to an outer surface of prefilled syringe 11, via collar 12, by way of the several mounting and connection methods discussed above. This method of assembly for a medical shield apparatus prevents disturbance of its component parts and advantageously avoids contamination thereof, particularly needle cannula 15, during manufacture.

Figure 9:
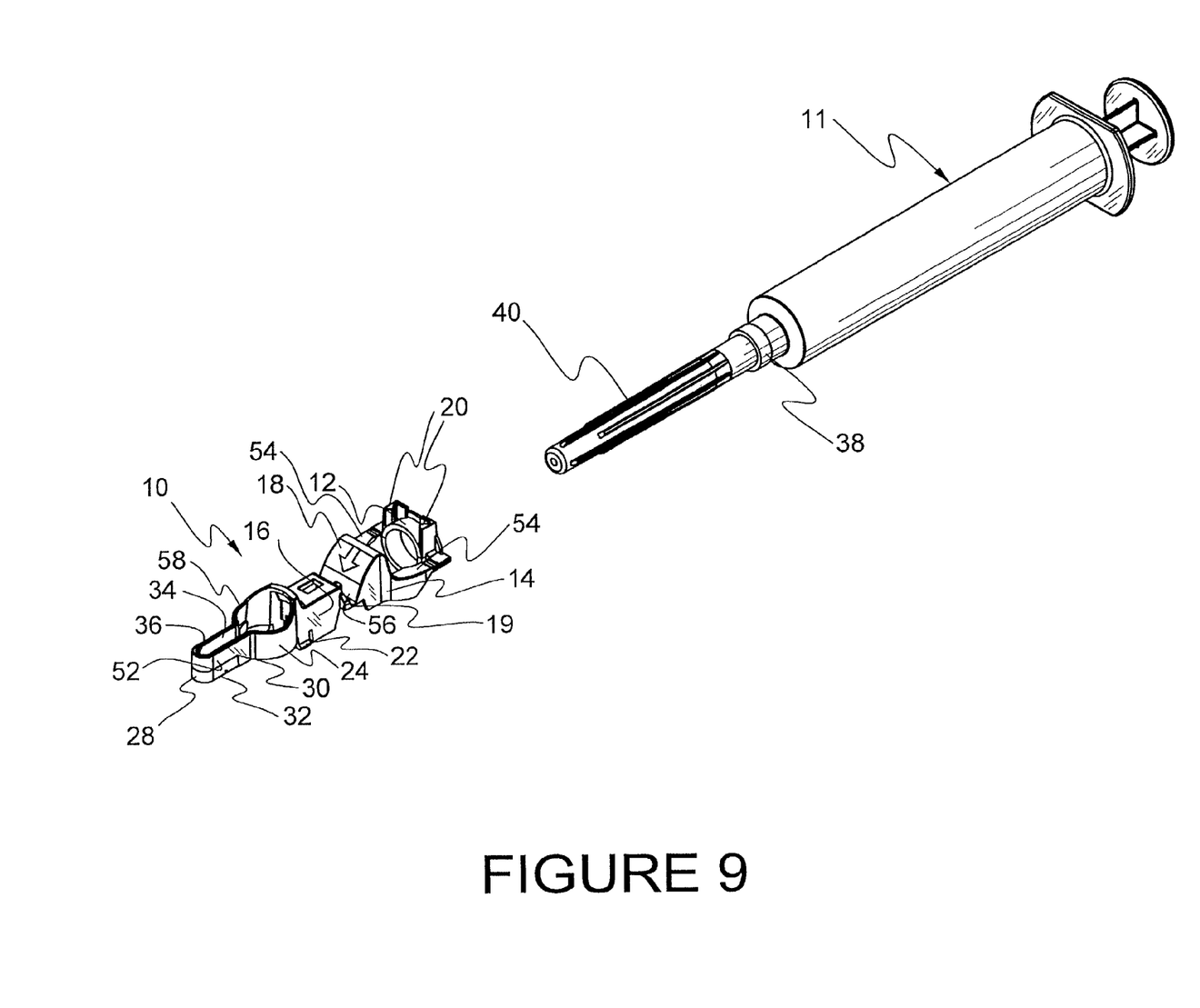
FIG. 9 is a perspective view of the safety shield apparatus shown in FIG. 1 separate from a prefilled syringe with a needle cover.
Figure 10:
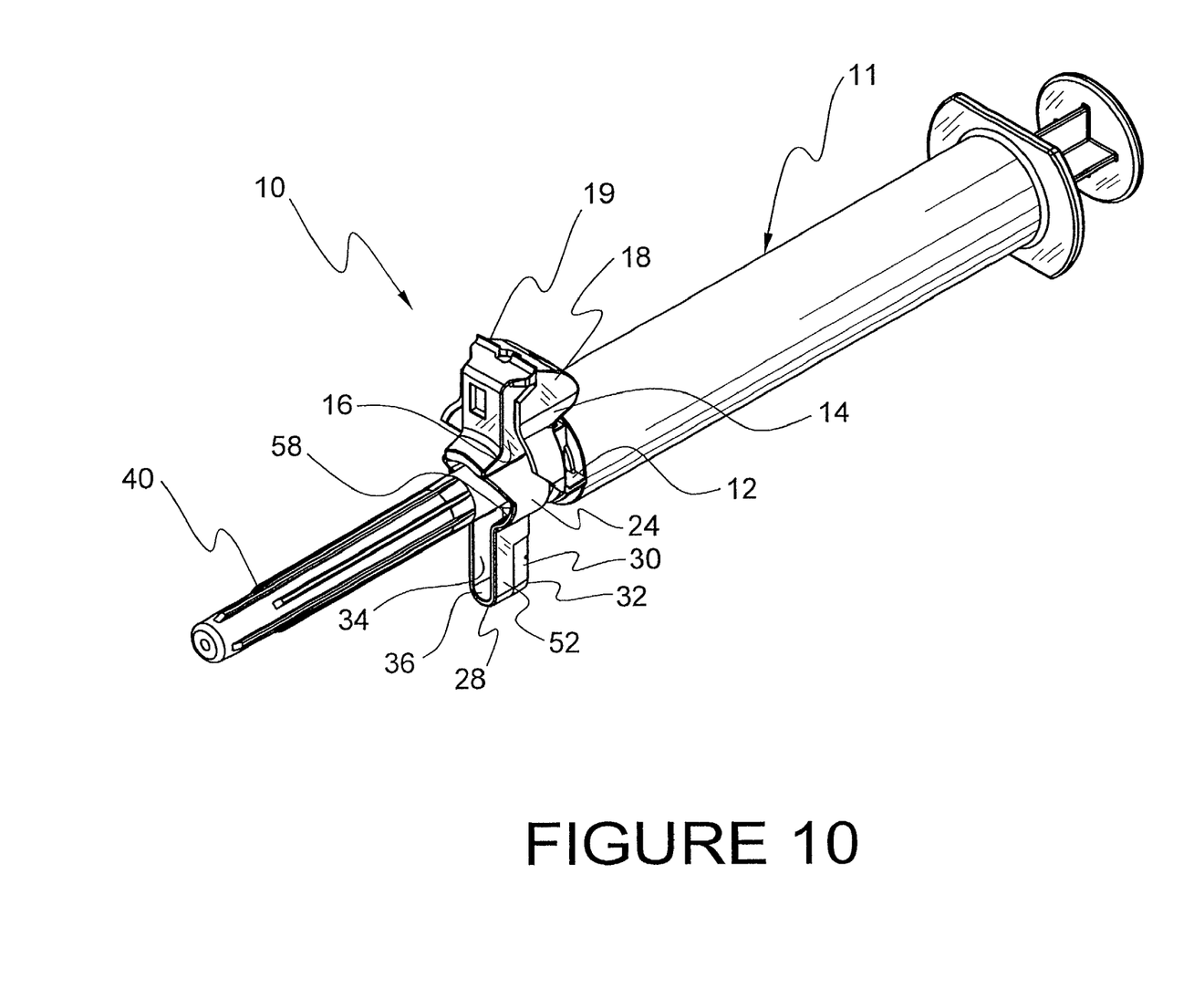
FIG. 10 is a perspective view of the safety shield apparatus attached to the prefilled syringe and the needle cover shown in FIG. 9.

In use, a medical needle shield apparatus similar to that described above, employing safety shield 10 and prefilled syringe 11, is properly sterilized and otherwise prepared for storage, shipment and use. As shown in FIGS. 9 and 10, a needle cover 40 is used to protect needle cannula 15. Needle cover 40 shields, prior to use and to prevent inadvertent unfolding or actuation, safety shield 10.

Safety shield 10 is in the retracted position. After completion of a medical procedure employing prefilled syringe 11, actuator 18 is manipulated such that latches 20 and catches 22 disengage. As safety shield 10 is urged from the retracted position to the extended position via one handed exertion on actuator 18, opening 58 of cylinder 24 travels about needle cannula 15. Wall 64 of fulcrum 60 engages needle cannula 15 to extend segments 14,16 and guide movement thereof, as discussed.

Needle cannula 15 becomes positioned within cavity 34 through channel 36 to engage base 32. Continued pressure exerted on actuator 18 and corresponding engagement of needle cannula 15 and base 32 disposes safety shield 10 in the extended position. In the extended position, nose portion 28 shields needle tip 17 in a protective configuration to prevent hazardous exposure thereto, providing security for a clinician and subject from accidental needle stick. As safety shield 10 is disposed in the extended position and needle cannula 15 and base 32 engage, lock 26 engages needle cannula 15 to non-releasably fix safety shield 10 in the protective configuration, as discussed.

The invention of the present disclosure may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A medical needle shield apparatus comprising:
    an extensible shield including a first segment and a second segment extending therefrom, the second segment including an opening configured for clearance of a medical needle of a medical needle device during attachment of the shield to the medical needle device, wherein the first segment is articulated to a collar mounted to the medical needle device; and
    the second segment defining a planar surface adjacent a distal portion thereof, the planar surface being configured to engage the needle for disposing the shield in an extended position, the second segment including a fulcrum disposed adjacent a proximal portion thereof, the fulcrum configured to engage the needle to facilitate extension of the shield from a retracted position to the extended position, wherein the fulcrum includes a slot configured to guide the needle therein during extension of the shield from the retracted position to the extended position.

2. A medical needle shield apparatus as recited in claim 1, wherein the apparatus is monolithically formed.

3. A medical needle shield apparatus as recited in claim 1, wherein the first segment has a pair of arms articulated to a collar mounted to a device supporting the needle.

4. A medical needle shield apparatus as recited in claim 1, wherein the collar is configured for mounting to a syringe.

5. A medical needle shield apparatus as recited in claim 1, wherein the collar includes a latch that engages the extensible shield to releasably lock the extensible shield in a retracted position.

6. A medical needle shield apparatus as recited in claim 5, wherein the latch engages a catch on the second segment to releasably lock the extensible shield in a retracted position.

7. A medical needle shield apparatus as recited in claim 1, wherein the collar includes a pair of latches disposed for engagement with a pair of catches of the second segment to releasably lock the extensible shield in a retracted position.

8. A medical needle shield apparatus as recited in claim 1, wherein the opening is configured for travel about the needle during extension of the shield.

9. A medical needle shield apparatus as recited in claim 1, wherein the second segment includes a nose portion which includes at least a portion of the planar surface.

10. A medical needle shield apparatus as recited in claim 9, wherein the nose portion defines a cavity for disposal of the needle therein.

11. A medical needle shield apparatus as recited in claim 10, wherein the cavity is defined by side walls and the planar surface of the nose portion.

12. A medical needle shield apparatus as recited in claim 1, wherein the second segment includes a lock that engages the needle to fix the shield in the extended position.

13. A medical needle shield apparatus as recited in claim 1, wherein the first segment includes a lock and the second segment includes a lock which cooperate to fix the shield in the extended position.

14. A medical needle shield apparatus as recited in claim 1, wherein the first segment includes a manual actuator configured to provide an engagement surface for manipulating the shield to the extended position.

15. A medical needle shield apparatus comprising:
    a syringe having a needle hub supporting a needle; and
    an extensible shield including a first segment and a second segment articulating therefrom, the first segment articulating from a collar disposed about the needle hub, the collar including a pair of latches; and
    the second segment defining an opening configured for travel about the needle to facilitate extension of the shield between a retracted position to an extended position the second segment further including a proximal fulcrum having a slot that engageably receives the needle to facilitate extension of the shield and a pair of catches;
    the catches being engageable with the latches to maintain the shield in the retracted position, the second segment having a nose portion defining a planar surface configured to engage the needle to facilitate disposing the shield in the extended position;
    the second segment further including a barbed flap lock that engages the needle and fixes the shield in the extended position.

* * * * *